United States Patent [19]

Seberg

[11] 4,300,553
[45] Nov. 17, 1981

[54] WINGED CATHETER PLACEMENT ASSEMBLY

[75] Inventor: Charles H. Seberg, Libertyville, Ill.

[73] Assignee: Abbott Laboratories, North Chicago, Ill.

[21] Appl. No.: 31,370

[22] Filed: Apr. 19, 1979

Related U.S. Application Data

[63] Continuation-in-part of Ser. No. 950,941, Oct. 12, 1978, Pat. No. 4,194,504.

[51] Int. Cl.³ ............................................. A61M 5/00
[52] U.S. Cl. .......................... 128/214.4; 128/DIG. 16
[58] Field of Search ............... 128/214 R, 214.4, 221, 128/347, 348

[56] References Cited

U.S. PATENT DOCUMENTS

| | | | |
|---|---|---|---|
| 3,064,648 | 11/1962 | Bujan | 128/214 |
| 3,123,072 | 3/1964 | Bellamy | 128/221 |
| 3,399,674 | 9/1968 | Pannier et al. | 128/214.4 |
| 3,537,451 | 11/1970 | Beck et al. | 128/214.4 |
| 3,589,361 | 6/1971 | Loper et al. | 128/214 |
| 4,177,809 | 12/1979 | Moorehead | 128/214.4 |
| 4,192,305 | 3/1980 | Seberg | 128/214.4 |
| 4,192,306 | 3/1980 | Genese | 128/214.4 |
| 4,194,504 | 3/1980 | Harms et al. | 128/214.4 |

FOREIGN PATENT DOCUMENTS 190388 12/1922 United Kingdom ............... 128/221

Primary Examiner—Dalton L. Truluck
Attorney, Agent, or Firm—Robert L. Niblack; Neil E. Hamilton; Robert S. Beiser

[57] ABSTRACT

A needle-inside, catheter placement assembly including needle and catheter units. The needle unit comprises a needle joined by a flexible line to a needle hub. The catheter unit comprises a catheter, winged catheter insertion means, flexible tubing and tube hub, wherein an area of reduced thickness on each wing of the insertion means provides improved flexibility for the wing. The needle is captured within the winged catheter insertion means when the wings are simultaneously held in a vertical position and axial and rotational alignment of the needle and catheter units are maintained by mechanically interlocked complementary means associated with the needle and lumen of the winged catheter insertion means.

6 Claims, 11 Drawing Figures

WINGED CATHETER PLACEMENT ASSEMBLY

This application is a continuation in part of U.S. Pat. No. 4,194,504, Winged Catheter Placement Assembly, application Ser. No. 950,941 filed Oct. 12, 1978, and issued Mar. 25, 1980.

BACKGROUND OF THE INVENTION

The present invention relates to intravenous catheter placement assemblies and, more particularly, to needle-inside, winged catheter placement assemblies.

U.S. Pat. No. 2,725,058 granted to A. Rathkey on Nov. 29, 1955 and U.S. Pat. No. 3,064,648 granted to A. Bujan on Nov. 20, 1962 disclose winged, intravenous needle assemblies. These needles serve as both a vein puncturing means and medical solutions conduit when used for intravenous solutions administration. Due to the necessary rigidity of these needles and their sharpened ends, it is common to immobilize that part of the patient into which the needle is inserted to avoid inadvertent damage to the patient's vein. If the needle remains inserted for extended periods of time, such continued immobilization results in stiffness and other discomfort to the patient.

U.S. Pat. No. 3,537,451 granted to D. Beck, et al., on Nov. 3, 1970, discloses a needle-inside catheter placement assembly having a partially rigid, partially flexible needle and a removeable, winged insertion means loosely surmounting the catheter. Unfortunately, once the winged insertion means has been removed from the catheter, it cannot be used for securing the inserted catheter to the flesh of the patient surrounding the venipuncture site.

U.S. Pat. No. 3,589,361 granted to D. Loper on June 29, 1971 discloses a needle-inside, winged catheter placement assembly which seeks to obviate the disadvantages of the Rathkey, Beck and Bujan needles. The Loper device comprises a needle concentrically located inside a flexible catheter which has a winged insertion means slidably affixed thereon and a hub affixed to its proximal end. When a patient is to be administered an intravenous solution, the winged insertion means is used to insert the needle and catheter into the patient's vein. The needle is then withdrawn from the catheter and the vein and the catheter adhered to the patient's body by means of the slidable wings.

An inherent disadvantage of the Loper device is that its catheter hub is located so near the venipuncture wound that inadvertent manipulation of the catheter can occur during attachment of the intravenous solution administration tubing to the hub, resulting in irritation of, or damage to, the tissue at the wound site. U.S. Pat. No. 3,769,975 granted Nov. 6, 1973 to M. Nimoy, et al. discloses a needle-inside, winged catheter placement assembly that obviates the above-stated inherent disadvantage of the Loper device by means of a flexible tubing extending from the proximal end of its winged insertion means and having a tubing hub at its proximal end.

An inherent disadvantage of the Nimoy device is that it requires the use of an extraneous sleeve positioned over the flexible tubing to prevent displacement of the wing section toward the tubing hub during the catheterization procedure. The need for such a sleeve requires additional costs and steps in the assembling and use of the Nimoy device. Another disadvantage of the Nimoy device is that its needle is rigid along its entire, relatively long length, resulting in poor maneuverability of the device during venipuncture. Accordingly, it will be apparent that such a needle-inside, winged catheter placement assembly without need of an extraneous sleeve and having a needle of substantially more flexibility would be advantageous and desirable.

SUMMARY OF THE INVENTION

Therefore, it is the primary object of this invention to provide a needle-inside, winged catheter placement assembly of the type disclosed by Nimoy, but without the need of an extraneous sleeve to prevent displacement of the winged catheter insertion means towards the tubing hub during the catheterization procedure and without a relatively long, rigid needle.

In accordance with these and other objects, there is provided by the present invention, a winged intravenous catheter assembly including needle and catheter units. The venipuncture unit comprises a relatively short rigid needle joined by a flexible line to a needle hub. The catheter unit comprises a flexible plastic catheter having a distally tapered distal end and a winged catheter insertion means including a tubular body having a lumen therethrough and a pair of wings extending oppositely therefrom. The proximal end of the catheter is in communication with the lumen of the catheter insertion means via its distal end. The catheter unit further comprises a flexible tubing having its distal end in communication with the lumen of the catheter insertion means via its proximal end and a tube hub having a lumen therethrough. The proximal end of the flexible tubing is in communication with the lumen of the tube hub via its distal end.

The needle unit is disposed within the catheter, winged catheter insertion means, flexible tubing and tube hub, with the sharpened distal end of the needle extending beyond the distal end of the catheter. Axial and rotational alignment of the needle and catheter units are maintained by mechanically interlocked complementary means associated with the needle and the lumen of the winged catheter insertion means.

Surprisingly, it has been found that the displacement of the winged catheter insertion means toward the tube hub present in the prior art devices is obviated by locking the winged catheter insertion means to the needle during the venipuncture. The temporary locking is achieved by providing the lumen of the winged catheter insertion means a diameter opposite a portion of the wings adjacent the tubular body that is predetermined to capture the needle unit within the tubular body by the distortion of the lumen thereof when the wings are simultaneously held in a substantially vertical position. An area of reduced thickness on each of the wings substantially adjacent to the tubular body provides improved flexibility to the wings.

BRIEF DESCRIPTION OF THE DRAWING

Other objects and attendant advantages will be obvious to those skilled in the art by reading the following detailed description in connection with the accompanying drawing wherein like reference characters designate like or corresponding parts throughout the several figures thereof and wherein.

DETAILED DESCRIPTION OF THE INVENTION

Figure 1:
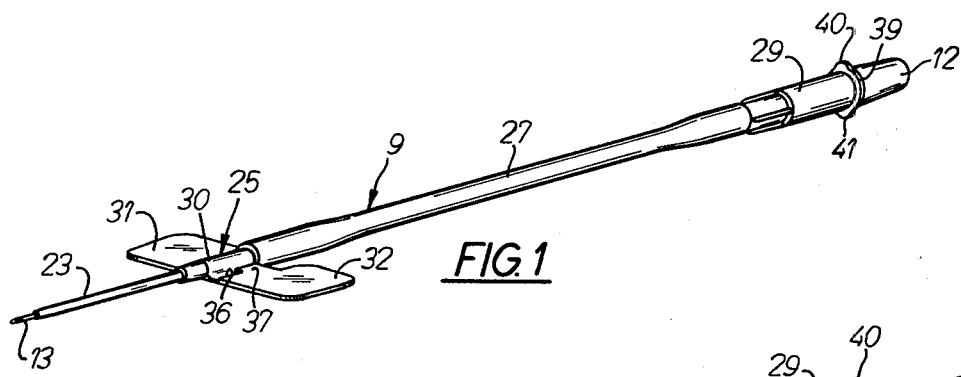
FIG. 1 is a perspective view of a preferred embodiment of the needle-inside, winged catheter placement assembly of the present invention.
Figure 2:
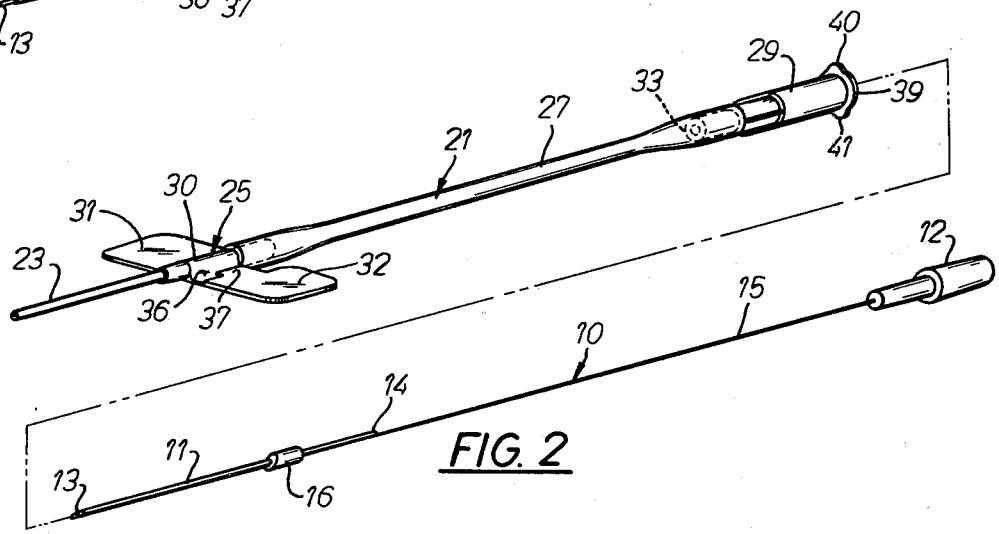
FIG. 2 is an exploded view of the assembly of FIG. 1 showing the catheter and needle units thereof.

Referring to the drawing, there is shown in FIG. 1 a preferred embodiment of the needle-inside, winged catheter placement assembly 9 of this invention. Winged catheter placement assembly 9 includes a needle unit 10 which comprises a needle 11 having its proximal end attached to a needle hub 12 by a flexible line 15 and a beveled, sharpened distal end 13, as best seen in FIG. 2.

Preferably, needle 11 is made of a hollow, cylindrical stainless steel tube. However, it will be readily apparent to those skilled in the art, that the perimeter of needle 11 can have various configurations, or even a plurality of configurations along its length, if so desired. Preferably, needle 11 will have an aperture 14 at its proximal end to allow the passage of blood from distal end 13 through aperture 14. Flexible line 15, preferably, can be made of stainless steel. However, flexible line 15 can also be made of any other suitable metal or plastics material. Needle hub 12, preferably, can be made of plastics, such as polyvinylchloride, ABS copolymers, or polycarbonate, and have a tapered distal end.

An orientation collar 16 is located on needle 11. Collar 16 is asymmetrical at its distal end and is generally disposed intermediate the proximal and distal ends of needle 11. Optionally collar 16 can extend beyond the proximal end of needle 11, if so desired. Preferably, collar 16 can be made of stainless steel, however, it can also be made of any other suitable metal or plastics material. Optionally, flexible line 15 can be attached to a portion of collar 16 as well as needle 11, if so desired.

Catheter placement assembly 9 further comprises a catheter unit 21 having a plastic catheter 23, winged catheter insertion means 25, flexible tubing 27 and tube hub 29. Catheter 23 is distally tapered at its distal end and can be made of any biocompatible flexible plastic material such as polyethylene, polypropylene, polytetrafluorethylene, polyfluorinated ethylene propylene, or polyvinylchloride. The inner diameter of catheter 23 is substantially identical to the outer diameter of the portion of needle 11 that it encircles.

Figure 3:
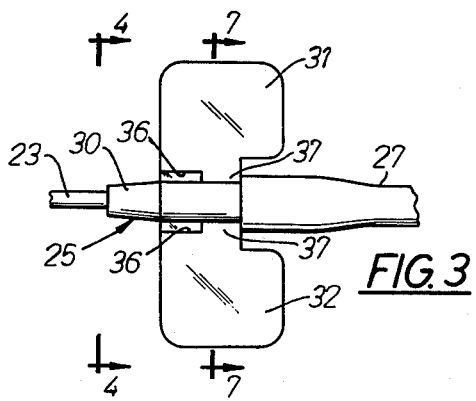
FIG. 3 is a top view of a portion of the assembly of FIG. 1 showing the reduced portions of the wings thereof.
Figure 4:
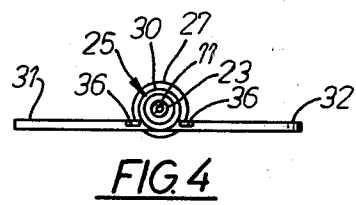
FIG. 4 is a cross-sectional view along the line 4—4 in FIG. 3 of the assembly thereof.

Winged catheter insertion means 25 has a tubular body 30 having a lumen therethrough and a pair of flexible wings 31, 32 oppositely extending therefrom. As shown in the embodiment of FIGS. 3 and 4, wings 31, 32 have substantially uniform thickness, except for an area of reduced thickness 36 along a portion of the width on each wing substantially adjacent to tubular body 30. The reduced thickness 36 provides improved flexibility for wings 31, 32 which otherwise tend to bow rather than bend when moved in a vertical direction.

Figure 5:
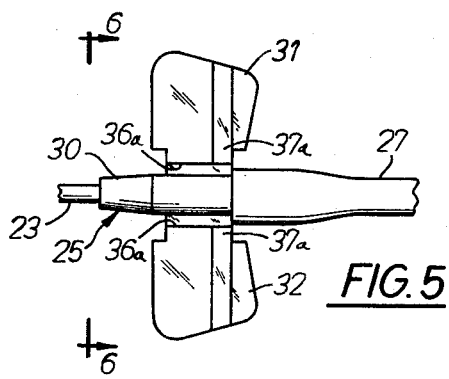
FIG. 5 is a top view of a portion of another embodiment of the winged catheter insertion means of the needle-inside, winged catheter placement assembly of the present invention showing the raised and reduced portions of the wings thereof.
Figure 6:
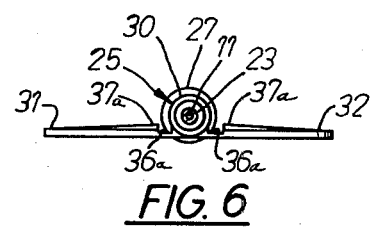
FIG. 6 is a cross-sectional view along the line 6—6 in FIG. 5 of the assembly thereof.

The remaining unreduced portions 37 of wings 31, 32 adjacent to tubular body 30, preferably, have the same thickness as the remainder of the wing. As illustrated in the embodiments of FIGS. 5 and 6, wings 31, 32 have substantially uniform thickness, except for an area of reduced thickness 36a along the entire width of each wing substantially adjacent to tubular body 30 and a raised portion 37a tapering away from and transverse to tubular body 30.

The proximal end of catheter 23 is in communication with the lumen of tubular body 30 of the winged catheter insertion means 25 via its distal end. The lumen of tubular body 30 has a diameter opposite, at least, the unreduced portions 37 or raised portion 37a of wings 31, 32 predetermined to only capture needle unit 10 within tubular body 30 by distortion of the lumen due to pressures from unreduced portion 37 or raised portion 37a when wings 31, 32 are simultaneously held in a substantially vertically position.

Figure 10:
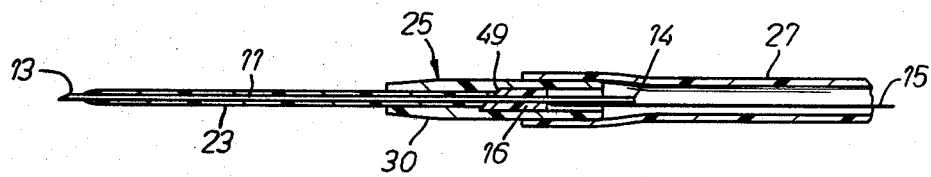
FIG. 10 is a cross-sectional view along a vertical plane through the axis of an embodiment of the winged catheter placement assembly of the present invention.
Figure 11:
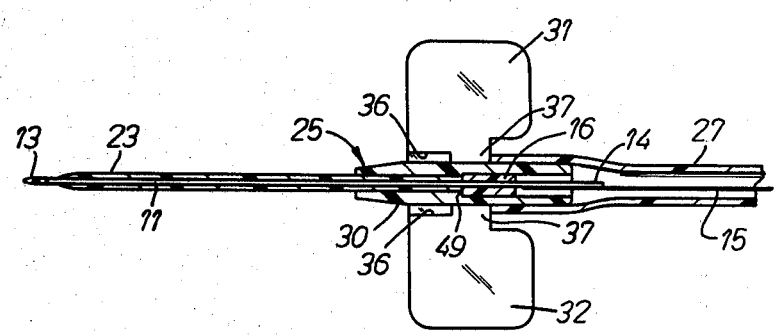
FIG. 11 is a cross-sectional view along a horizontal plane through the axis of a winged catheter placement assembly having a winged catheter insertion means of the type illustrated in FIG. 3.

Preferably, as shown in FIGS. 10 and 11, the predetermined diameter of the lumen of tubular body 30 will also be complementary to collar 16 on needle 11. Therefore, needle unit 10 is preferably captured along at least a portion of collar 16 when the lumen of tubular body 30 is distorted by the simultaneous holding of wings 31, 32 in a vertical position. Further, the complementary portions of collar 16 and the lumen of tubular body 30 that are asymmetrical serve to mechanically interlock and orient the needle and catheter units in distally axial and rotational alignment. While such asymmetrical portions will generally be at the distal end of collar 16, they can occur at other portions thereof, if so desired.

Figure 7:
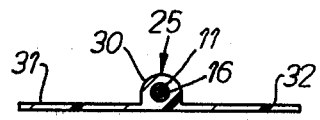
FIG. 7 is a cross-sectional view along the line 7—7 in FIG. 3 of the assembly thereof when the wings are in a horizontal position.
Figure 8:
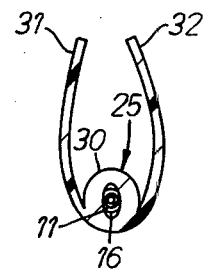
FIG. 8 shows the assembly of FIG. 7 when the wings thereof have been simultaneously raised to a substantially vertical position.
Figure 9:
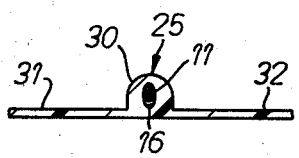
FIG. 9 is a cross-sectional view similar to FIG. 7 wherein the lumen of the winged catheter insertion means is noncylindrical when the wings are in a horizontal position.

As illustrated in FIGS. 7-9, needle 11 and collar 16 have an outer diameter substantially identical to the surrounding diameter of the lumen of tubular body 30 when wings 31, 32 are horizontal. When wings 31, 32 are simultaneously held in a substantially vertical position, the diameter of the lumen of tubular body 30 is decreased horizontally due to distortion and needle 11 and collar 16 are captured therein. While collar 16 and the lumen of tubular body 30 can be cylindrical, it will be apparent to those skilled in the art that either or both of them can be noncylindrical, so long as their diameters are predetermined to capture needle 11 and/or collar 16 when wings 31, 32 are simultaneously held in a substantially vertical position, as shown in FIG. 9.

As illustrated in FIGS. 10 and 11, the predetermined, complementary diameter of the lumen of tubular body 30 opposite unreduced portions 37 or raised portions 37a of wings 31, 32 can be formed as an integrally molded recess 49 in the wall of tubular body 30.

As shown in FIG. 1, catheter 23 has an outer diameter substantially equal to the inner diameter of the lumen of tubular portion 30 and is inserted therein. However, it will be readily apparent that tubular portion 30 can be designed to receive catheter 23 on its outer diameter, if so desired. The distal end of flexible tubing 27 is in fluid communication with the lumen of tubular portion 30 at its proximal end. As shown in FIG. 1, tubular portion 30 is inserted into flexible tubing 27, but it will be readily apparent that flexible tubing 27 can be inserted into tubular portion 30, if so desired. Preferably, flexible tubing 27 can be made of clear polyvinylchloride or polyurethane and has an inner diameter greater than the inner diameter of catheter 23.

The proximal end of flexible tubing 27 is connected in fluid communication to tube hub 29 which has a lumen 33 therethrough. Tube hub 29 is, preferably, made of polyvinylchloride, ABS copolymers or polycarbonate and, preferably, has a recess or female luer adapter at its proximal end. A collar 39 having ears 40, 41 extends outwardly from the proximal endwall of tube hub 29.

When assembled, needle unit 10 is inserted into catheter unit 21 until needle orientation collar 16 can advance no further into winged insertion means 25. The distal end of needle hub 12 will be inserted into the proximal end of catheter hub 29. At that time, the bevel at distal end 13 of needle 11 will be oriented so that it is facing upwardly and projecting from the distal end of catheter 23 a chosen predetermined distance. The proximal end of needle 11 and aperture 14, if present, will then be situated within flexible tubing 27.

In use, it is anticipated that the catheter placement assembly 9 will be used to insert catheter 23 into a patient by pinching flexible wings 31, 32 together and inserting the distal end of needle 11 and catheter 23 into the patient's vein in accordance with conventional venipuncture techniques well known in the medical practice. During the venipuncture procedure, flexible line 15 and flexible tubing 27 can be held in any convenient position desired. After the vein has been entered, if needle 11 is hollow and has an aperture 14, it will allow blood to flow, or flashback, to flexible tubing 27 where it will readily be visible to indicate that the vein has been entered.

After placement of catheter 23 into the vein has been achieved, the device operator person inserting the assembly into the patient presses wings 31, 32 flat against the patient with one hand and uses the other hand to grasp needle hub 12. Needle unit 10 is now free to be withdrawn from catheter unit 21 and discarded by a gentle pull on needle hub 12. Catheter 23 will have been fully inserted into the vein, wings 31, 32 taped to the patient, a safety loop formed with flexible tubing 27 and an intravenous solution set attached to tube hub 29 in accordance with conventional techniques of the medical practice.

Having described the invention in specific detail and exemplified the manner in which it may be carried into practice, it will now be readily apparent to those skilled in the art that innumerable variations, applications, modifications and extensions of the basic principles involved may be made without departing from its sphere or scope.

I claim:

1. In an intravenous catheter assembly including (1) a catheter unit comprising:
    (a) a flexible plastic catheter having a distally tapered distal end,
    (b) a winged catheter insertion means comprising a tubular body having a lumen therethrough and a pair of wings having substantially uniform thickness extending oppositely therefrom, the proximal end of said catheter in communication with said lumen of said catheter insertion means via its distal end,
    (c) a flexible tubing having its distal end in communication with said lumen of said catheter insertion means via its proximal end,
    (d) a tube hub having a lumen therethrough, the proximal end of said flexible tubing in communication with said lumen of said tube hub via its distal end, and (2) a needle unit inserted through said catheter, winged catheter insertion means, flexible tubing and tube hub; the improvement which comprises:
    said needle unit comprising a needle having a sharpened distal end extending beyond said distal end of said catheter, and a flexible stylet joining the proximal end of said needle to the distal end of a needle hub,
    complementary means associated with said lumen of said winged catheter insertion means and said needle mechanically interlocked to provide distally axial and rotational alignment of said needle relative to said catheter unit, and
    an area of reduced thickness on each of said wings along at least a portion of the width thereof substantially adjacent to said tubular body and providing improved flexibility to said wings, said lumen of said winged catheter insertion means having a diameter predetermined to only capture said needle within said tubular body by the distortion of said lumen of said winged catheter insertion means when said wings are simultaneously held in a substantially vertical position.

2. The catheter assembly defined in claim 1, wherein said complementary means include a collar on said needle, said collar being asymmetrical at its distal end.

3. The catheter assembly defined in claim 1 or 2, wherein said complementary means include an asymmetrical recess molded into said lumen of said tubular body.

4. The catheter assembly defined in claim 3 wherein each of said wings has a raised portion transverse to said tubular body which raised portions exert pressure on said tubular body that distort the lumen thereof when said wings are simultaneously held in a substantially vertical position.

5. The catheter assembly defined in claim 3, wherein said lumen through said tubular body is noncylindrical when said wings are simultaneously disposed in a horizontal plane.

6. The catheter assembly defined in claim 3, wherein said needle unit further comprises an aperture intermediate of its proximal and distal ends through which blood can flow out of said needle into said flexible tubing.

* * * * *

UNITED STATES PATENT AND TRADEMARK OFFICE
CERTIFICATE OF CORRECTION

PATENT NO. : 4,300,553
DATED : November 17, 1981
INVENTOR(S) : Charles H. Seberg, Jack L. Harms It is certified that error appears in the above—identified patent and that said Letters Patent is hereby corrected as shown below:

On the title page, Item /75/ Inventor add,
and Jack L. Harms, Mundelein, Ill.

Signed and Sealed this

Twenty-sixth Day of July 1983.

[SEAL]

Attest:

GERALD J. MOSSINGHOFF

Attesting Officer      Commissioner of Patents and Trademarks